US00PP29547P2

(12) United States Plant Patent
Nguyen

(10) Patent No.: US PP29,547 P2
(45) Date of Patent: Jul. 24, 2018

(54) ***CALIBRACHOA* PLANT NAMED 'BALCANUMBI'**

(50) Latin Name: *Calibrachoa x hybrida*
Varietal Denomination: Balcanumbi

(71) Applicant: Ball Horticultural Company, West Chicago, IL (US)

(72) Inventor: Phuong N. Nguyen, Thousand Oaks, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/530,784

(22) Filed: Feb. 28, 2017

(51) Int. Cl.
*A01H 5/02* (2018.01)

(52) U.S. Cl.
USPC ..... Plt./413

(58) Field of Classification Search
USPC ..... Plt./413
CPC . A01H 5/02; A01H 5/025; A01H 5/12; A01H 5/00
See application file for complete search history.

(56) References Cited

U.S. PATENT DOCUMENTS 9,313,959 B2 * 4/2016 Sakazaki ..... A01H 5/02
PP27,008 P2 * 8/2016 Sakazaki ..... A01H 5/02 Plt./413

* cited by examiner

*Primary Examiner* — June Hwu
(74) *Attorney, Agent, or Firm* — Audrey Charles

(57) ABSTRACT

A new and distinct cultivar of *Calibrachoa* plant named 'Balcanumbi', characterized by its medium pink, dark red-purple and yellow tricolored flowers with the yellow coloration forming a central star pattern, medium green-colored foliage, and vigorous, mounded-trailing growth habit, is disclosed.

1 Drawing Sheet

Latin name of genus and species of plant claimed: *Calibrachoa* x *hybrida*.

Variety denomination: 'Balcanumbi'.

BACKGROUND OF THE INVENTION

The present invention relates to a new and distinct cultivar of *Calibrachoa* plant botanically, known as *Calibrachoa* x *hybrida* and hereinafter referred to by the cultivar name 'Balcanumbi'.

The new cultivar originated in a controlled breeding program in Arroyo Grande, Calif. during March 2014. The objective of the breeding program was the development of *Calibrachoa* cultivars with unique flower coloration and mounded-trailing growth habit.

The new *Calibrachoa* cultivar is the result of cross-pollination. The female (seed) parent of the new cultivar is the proprietary *Calibrachoa hybrida* breeding selection coded PN10583-2, not patented, characterized by its medium orange-colored flowers, medium green-colored foliage, and moderately vigorous, compact-mounded growth habit. The male (pollen) parent of the new cultivar is the proprietary *Calibrachoa hybrida* breeding selection coded PN10645-2, not patented, characterized by its medium purple-colored flowers, medium green-colored foliage, and moderately vigorous, mounded growth habit. The new cultivar was discovered and selected as a single flowering plant within the progeny of the above stated cross-pollination during August 2014 in a controlled environment in Arroyo Grande, Calif.

Asexual reproduction of the new cultivar by terminal stem cuttings since August 2014 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcanumbi' as a new and distinct cultivar of *Calibrachoa* plant:

1. Medium pink, dark red-purple and yellow tricolored flowers with the yellow coloration forming a central star pattern;
2. Medium green-colored foliage; and
3. Vigorous, mounded-trailing growth habit.

Plants of the new cultivar differ from plants of the female and male parents primarily in having a different flower color and flower color pattern, and in having increased growth vigor.

Of the many commercially available *Calibrachoa* cultivars, the most similar in comparison to the new cultivar is SUPERBELLS Evening Star 'USCAL42202' U.S. Pat. No. 9,313,959 and U.S. Plant Pat. No. 27,008. However, in side by side comparisons, plants of the new cultivar differ from plants of 'USCAL42202' in at least the following characteristics:

1. Plants of the new cultivar have a flower color that is different, from plants of 'USCAL42202', as plants of 'USCAL42202' have violet-colored flowers with a dark purple center and a yellow-colored star pattern, and plants of the new cultivar have medium pink-colored flowers with a dark red-purple center and a yellow-colored star pattern; and 2. Plants of the new cultivar have larger diameter flowers than plants of 'USCAL42202'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcanumbi'. The plants were grown in 4.5-inch pots for 9 weeks in a greenhouse in West Chicago, Ill. Plants were given one pinch one week after transplant.

DETAILED BOTANICAL DESCRIPTION

Figure 1:
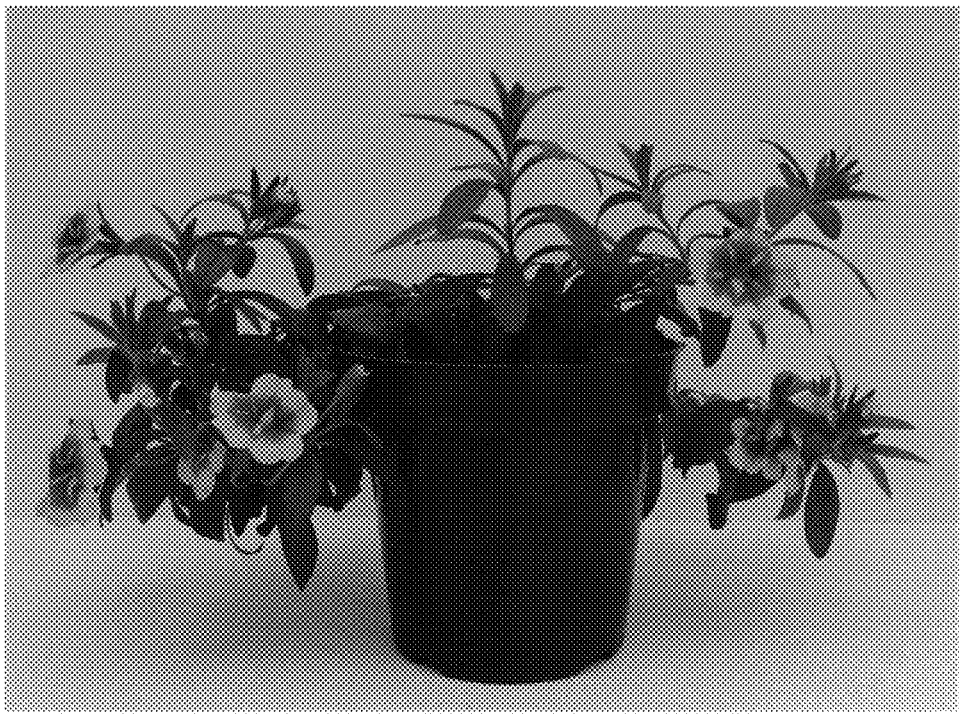
FIG. 1 illustrates a side view of the overall growth and flowering habit of 'Balcanumbi'.
Figure 2:
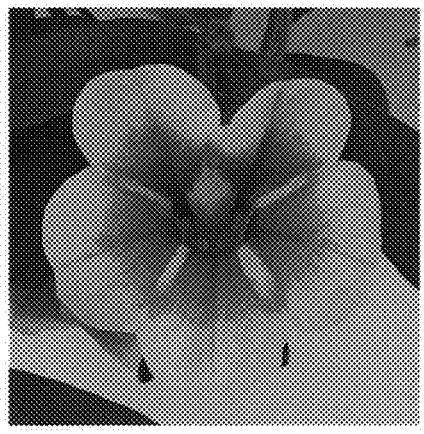
FIG. 2 illustrates a close-up view of an individual flower of 'Balcanumbi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2017 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 9 weeks utilizing a soilless growth medium. Plants were given one pinch one week after transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Calibrachoa* x *hybrida* cultivar Balcanumbi.

Parentage:

*Female parent*.—Proprietary *Calibrachoa* x *hybrida* breeding selection coded PN10583-2, not patented.

*Male parent*.—Proprietary *Calibrachoa* x *hybrida* breeding selection coded PN10645-2, not patented.

Propagation:

*Type cutting*.—Terminal stem.

*Time to initiate roots*.—Approximately 6 to 8 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 9 weeks from a rooted cutting to finish in a 10 cm pot.

*Growth habit and general appearance*.—Vigorous, mounded-trailing.

*Size*.—Height from soil level to top of plant plane: Approximately 9.5 cm. Width: Approximately 27.5 cm.

*Branching habit*.—Freely branching, pinching enhances basal branching. Quantity of main branches per plant: Approximately 5.

*Branch*.—Strength: Moderate. Length: Approximately 14.0 cm. Diameter: Approximately 2.0 mm. Length of central internode: Approximately 9.0 mm. Texture: Densely glandular pubescent. Gland color: Colorless, transparent. Color of young and mature stems: 144A.

Foliage description:

*General description*.—Quantity of leaves per main branch: Approximately 19. Fragrance: Slight. Form: Simple. Arrangement on flowering stem: Alternate.

*Leaves*.—Aspect: At acute angle to stem with tip turning downward. Shape: Elliptic. Margin: Entire. Apex: Broadly acute. Base: Attenuate. Venation pattern: Pinnate. Length of mature leaf: Approximately 3.7 cm. Width of mature leaf: Approximately 1.2 cm. Texture of upper and lower surfaces: Moderately glandular pubescent. Gland color: Colorless, transparent. Color of upper surface of young foliage: 137B with midvein of 144D. Color of lower surface of young foliage: Closest to 138A with midvein of 138B. Color of upper surface of mature foliage: 137A with venation of 144A to indistinguishable. Color of lower surface of mature foliage: Between 138A and 138B with venation of 138D to indistinguishable.

*Petiole*.—Length: Approximately 3.0 mm. Diameter: Approximately 1.0 mm. Texture: Moderately glandular pubescent. Gland color: Colorless, transparent. Color: 144A.

Flowering description:

*Flowering habit*.—'Balcanumbi' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, salverform. Quantity per plant: Approximately 10. Fragrance: None detected.

*Bud*.—Rate of opening: Generally takes 3 to 4 days for bud to progress from first color to fully open flower. Quantity per plant: Approximately 8.

*Bud just before opening*.—Shape: Oblong. Length: Approximately 1.8 cm. Diameter: Approximately 5.0 mm. Texture: Densely glandular pubescent. Gland color: Colorless, transparent. Color: Petal portion 155A tinted with N187D, tube portion 154B, venation of N77A.

*Corolla*.—Diameter: Approximately 3.3 cm.

*Petals*.—Quantity: 5, fused to form a tube. Shape: Obovate. Margin: Entire. Apex: Obtuse to shallowly knotched. Length from tube: Approximately 1.2 cm. Length of free portion: Approximately 5.0 mm, moderate lobing. Width: Approximately 1.5 cm. Texture of upper surface: Glabrous. Texture of lower surface: Glandular pubescent, dense along venation. Gland color: Colorless, transparent. Color of upper surface when first and fully open: Upper half of petals N74D with lower half of N78A and N74A, petal margins of lower half 7B having the overall appearance of a star pattern, midveins of N82C. Color of lower surface when first and fully open: 76C with midveins of N77A. Conspicuousness of venation: Very weak, only midveins visible.

*Corolla tube*.—Length: Approximately 1.9 cm. Diameter at distal end: Approximately 6.0 mm. Diameter at proximal end: Approximately 1.0 mm. Texture of inner surface: Glabrous. Texture of outer surface: Densely glandular pubescent. Gland color: Colorless, transparent. Color of inner surface: 1A with weak venation and throat opening of N77A. Color of outer surface: Lighter than 154C with moderate venation of N77A.

*Sepals*.—Quantity per flower: 5, fused along lower half. Shape: Lanceolate. Apex: Acute. Length: Approximately 1.5 cm to 1.8 cm. Width: Approximately 4.0 mm to 5.0 mm. Texture of upper and lower surfaces: Densely glandular pubescent. Gland color: Colorless, transparent. Color of upper surface: 137A. Color of lower surface: 138B with base of 144B.

*Peduncle*.—Strength: Strong, flexible. Aspect: Acute angle to stem. Length: Approximately 3.0 cm. Diameter: Approximately 1.0 mm. Texture: Densely glandular pubescent. Gland color: Colorless, transparent. Color: 144A.

*Reproductive organs*.—Androecium: Stamen quantity: 5, basifixed. Stamen length: Approximately 1.1 cm. Filament length of fixed portion: Approximately 5.0 mm. Filament color: 155A. Anther shape: Bilobed, ovoid. Anther length: Approximately 1.0 mm. Anther color: 8A. Pollen amount: Abundant. Pollen color: 8C. Gynoecium: Pistil quantity: 1 per flower. Pistil length: Approximately 1.1 cm. Stigma shape: Funnel. Stigma length: Less than 1.0 mm. Stigma color: 143A. Style length: Approximately 9.0 mm. Style color: 145D. Ovary diameter: Approximately 2.0 mm. Ovary color: 144A.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcanumbi', substantially as herein illustrated and described.

* * * * *